United States Patent [19]

Yoshigi et al.

[11] Patent Number: 4,591,561
[45] Date of Patent: May 27, 1986

[54] PROCESS FOR THE PREPARATION OF MALTOPENTAOSE

[75] Inventors: Naohiro Yoshigi; Takahide Chikano; Yoshitada Mori, all of Tokyo, Japan

[73] Assignee: Sapporo Breweries Limited, Tokyo, Japan

[21] Appl. No.: 527,181

[22] Filed: Aug. 26, 1983

[30] Foreign Application Priority Data

Sep. 13, 1982 [JP] Japan .................. 57-158099

[51] Int. Cl.$^4$ .................. C12P 19/04; C12P 19/14; C12R 1/085
[52] U.S. Cl. .................. 435/101; 435/99; 435/834
[58] Field of Search .................. 435/101, 99, 202, 834, 435/832

[56] References Cited

U.S. PATENT DOCUMENTS 3,808,102  4/1974  Douros et al. .................. 435/202
4,039,383  8/1977  Pankratz .................. 435/99

OTHER PUBLICATIONS

*Archives of Biochemistry & Biophysics*, vol. 155, 290–298, (1973), "A Thermophilic Extracellular α-Amylase from *Bacillus licheniformis*.", Narimasa Saito.

*Primary Examiner*—Thomas G. Wiseman
*Assistant Examiner*—Rebecca L. Thompson
*Attorney, Agent, or Firm*—Frishauf, Holtz, Goodman & Woodward

[57] ABSTRACT

A process for the preparation of maltopentaose is disclosed, comprising cultivating a maltopentaose-producing microorganism belonging to a genus Bacillus in a medium and isolating the thus-accumulated maltopentaose from the culture broth. A typical example of the maltopentaose-producing microorganism is *Bacillus cereus* NY-14. This process permits the preparation of maltopentoase without the use of amylase as in conventional methods. Maltopentaose is useful, for example, as a substrate for the determination of serum amylase.

10 Claims, No Drawings

PROCESS FOR THE PREPARATION OF MALTOPENTAOSE

FIELD OF THE INVENTION

The present invention relates to a process for preparing maltopentaose by cultivating a maltopentaose-producing microorganism belonging to the genus Bacillus in a medium.

BACKGROUND OF THE INVENTION

Maltopentaose has heretofore been prepared by hydrolysis of starch or amylose utilizing various amylases. This method of preparation, however, suffers from disadvantages in that it is necessary to prepare the necessary amylases, and the hydrolyzate contains large amounts of maltooligosaccharides other than maltopentaose, making purification of maltopentaose very difficult.

Maltopentaose is now widely used, for example, as a substrate for the determination of serum amylase. Thus, mass-production of maltopentaose is expected. However, as described above, this cannot be realized by the conventional method of preparation.

SUMMARY OF THE INVENTION

According to the present invention, it has now been found that when *Bacillus cereus* NY-14 isolated from a soil is cultivated in a medium which contains soluble starch, etc. as carbon source under aerobic conditions, a large amount of maltopentaose is accumulated in the culture broth.

The present invention provides a process for preparing maltopentaose which comprises cultivating a maltopentaose-producing microorganism belonging to the genus Bacillus in the medium to accumulate maltopentaose in the culture broth, and isolating the maltopentaose thus accumulated from the culture broth.

DETAILED DESCRIPTION OF THE INVENTION

Any microorganism belonging to the genus Bacillus and capable of producing maltopentaose can be used in the invention. A typical strain is *Bacillus cereus* NY-14 which has been isolated from a soil by the inventors.

Microbial characteristics of *Bacillus cereus* NY-14 are as follows:

(I) Morphological Characteristics (1) Form and size of cell

Cells which were cultivated in a 0.5% sodium chloride bouillon medium under aerobic condition at 30° C. for 24 hours are long rods measuring $1\mu \times 3.0-4.0\mu$ in size and exist singly or in short chains comprising two or more, in some cases, five or six thereof.

(2) Motility

No motility. No flagella.

(3) Formation of spore

Spore formation occurs. The spore is ellipsoidal, measuring $0.7-0.8\mu$, and is present in the center or the paracenter. The sporangia is not swollen.

(4) Gram-staining

Positive

(II) Culture Characteristics (1) Bouillon agar plate culture (30° C., 48 hours)

Colonies are spreading. The surface is flat and rough. The margin is auriculate and arborescent white.

(2) Bouillon agar slant culture (30° C., 48 hours)

Growth is abundant. The surface is rough, opaque, and spreading. The margin is lobate. Nonsticking.

(3) Bouillon stab culture (30° C., 5 days)

Growth is abundant over the entire surface. Grows only along the line of the stab.

(4) Bouillon broth (30° C., 5 days)

Growth is good. The liquid is transparent, and sediments are formed. No pellicle is formed. An easily disporsed ring is formed. No pigment is formed.

(5) 0.5% Sodium chloride bouillon agar plate culture (30° C., 48 hours)

Colonies are irregular in form. The surface is flat and rough. The margin is auriculate and arborescent white. No comma-shaped colony is formed.

(6) 0.5% Sodium chloride bouillon agar slant culture (30° C., 48 hours)

Growth is abundant. The surface is rough, opaque, and spreading. The margin is lobate. Nonsticking.

(7) 0.5% Sodium chloride bouillon stab culture (30° C., 5 days)

Growth is abundant over the entire surface. Grows only along the line of the stab.

(8) 0.5% Sodium chloride bouillon broth (30° C., 5 days)

Growth is good. The liquid is turbid, and sediments are formed. Neither pellicle nor pigment is formed.

(9) Milk agar streak plate (30° C., 24 hours)

The zone of hydrolysis of casein is wide.

(10) Bouillon gelatin stab culture (20° C., 7 days)

Liquefaction occurs rapidly in the crateriform or stratiform.

(III) Physiological Characteristics (1) Reduction of Nitrate to Nitrite: positive (2) Voges-Proskaner Test: positive (3) Methyl Red Test: positive (4) Utilization of Citrate: positive (5) Production of Indole: negative (6) Production of Hydrogen Sulfide: positive (7) Production of Ammonia: positive (8) Milk reaction: Coagulation (9) Catalase: positive

(10) Growth Ranges: pH; 5.2–10.2, temperature; 7°–37° C.

(11) Oxygen relation: aerobic and produces glucose under anaerobic conditions.

(12) O-F Test: decomposes saccharide (glucose), producing acid under anaerobic conditions.

(13) Growth in Sabouraud Dextrose Culture Broth /Agar Slant

Culture: positive

(14) Production of Acid and Gas from Carbohydrates: Not grow in D-xylose, L-arabinose, L-rhamnose, mannitol, D-raffinose, glycerol, D-galactose, D-mannose, lactose, and sucrose.

Grow in soluble starch, D-glucose, D-fructose, trehalose, salicin, and maltose, producing acid, but not gas.

(15) Growth in 0.001% Lysozyme: positive

(16) Growth in 0.02% Azide: positive

(17) Growth in 7% NaCl: positive

As a result of a comparative study on the above-described characteristics with reference to *Bergey's Mannual of Determinative Bacteriology*, 8th ed. (1974), this strain was identified as *Bacillus cereus* and thus it was named *Bacillus cereus* NY-14. This strain has been deposited in the Fermentation Research Institute, Agency of Industrial Science and Technology, Ministry of International Trade and Industry of Japan under the accession number of FERM BP-329. In the present invention, as described above, any microorganism can be used as long as it belongs to the genus Bacillus and is capable of producing maltopentaose. Hence it is to be noted that the present invention is not limited to *Bacillus cereus* NY-14, and its variants and mutants.

In the preparation of maltopentaose by the process of the invention, the above-described strain is cultivated in a medium containing nutrients assimilable by known microorganisms. In greater detail, this preparation of maltopentaose needs polysaccharides having α-1,4-glucosidic linkage, for example, various starches such as potato starch, corn starch, rice starch, barley starch, wheat starch, sweet potato starch, etc.; soluble starch; amylopectin; amylose and dextrin. Hence the medium to be used in the cultivation of *Bacillus cereus* NY-14 contains one or more of such polysaccharides, and additionally, other various intredients required for the growth thereof, for example, an organic or inorganic nitrogen source, organic or inorganic salts, and vitamins.

Cultivation conditions vary with the type of the strain, etc., but should be determined so that the production of the desired maltopentaose reaches a maximum. In the case of cultivation of *Bacillus cereus* NY-14, it is suitable that the pH is from 5.5 to 9.0, preferably from 7.0 to 8.0, the cultivation temperature is from 20° to 37° C., preferably from 25° to 30° C., and the cultivation time is from 24 to 168 hours, preferably from 48 to 72 hours, and it is preferred for the cultivation to be performed under aerobic conditions.

The amount of polysaccharide being added to the medium is from 0.5 to 40%, and preferably from 2.5 to 4%. By-production of maltotetraose, maltohexaose, etc. is greatly reduced, when the amount is within the preferred range.

Separation of maltopentaose from the culture broth after the cultivation and its purification can be performed by suitable known techniques. For example, the culture broth is filtered by any suitable method to obtain a filtrate, and the filtrate is then subjected to a chromatographic treatment, such as gel filtration and ion exchange, to obtain a purified product of maltopentaose.

In accordance with the process of the invention, as described above, maltopentaose can be efficiently prepared without being attended with problems such as an additional step of preparation of amylase as in the conventional method and difficulty of purification. Hence the present invention permits the mass-production of maltopentaose and increases the field of its use.

The present invention is described in greater detail by reference to the following examples.

The amount of carbohydrate was determined by the phenolsulfuric acid method and indicated in the amount as calculated as glucose.

Analysis of saccharide was performed by the following paper chromatographic analysis:

A given amount of saccharide-containing solution was spotted on Toyo filter paper No. 50 (19×19 cm) and developed twice in a closed chamber at 70° C. by the ascending method with 65% n-propyl alcohol as a solvent. After development, each oligosaccharide was hydrolyzed by treating with glucoamylase at 40° C. for 30 minutes and detected by the silver nitrate dip technique.

The amount of maltopentaose prepared was measured as follows:

The culture broth was developed by paper chromatography in the same manner as in the analysis of saccharide and, thereafter, was subjected to a glucoamylase treatment. A part corresponding to the maltopentaose fraction was cut off and extracted with hot water at 100° C. for 15 minutes. The extract thus obtained was measured for the amount of maltopentaose (calculated as glucose) by the phenol-sulfuric acid method.

EXAMPLE 1

Ten milliliters of a medium (pH: 8.0) containing 3.5% soluble starch, 1% peptone, and 0.5% NaCl in tap water was placed in a test tube (diameter: 21 millimeters; length: 210 millimeters) and sterilized at 121° C. for 10 minutes. *Bacillus cereus* NY-14 (deposited in the Fermentation Research Institute, Japan, under the accession number of FERM BP-329), was picked up from the agar slant, and innoculated into a test tube. The incubation was carried out at 30° C. for 24 hours on a reciprocating shaker (250 strokes per minute, 20 millimeters amplitude).

After incubation the culture broth was centrifuged at 4° C. at 15,000 rpm to remove the bacterial cells. In the thus-obtained supernatant, the concentration of carbohydrate was 24.1 milligrams per milliliter and the concentration of maltopentaose was 9.0 milligrams per milliliter, and 37% of the residual saccharides could be accumulated as maltopentaose.

Paper chromatographic analysis confirmed that maltopentaose existed as a single spot.

Ten milliliters of the above-obtained supernatant was applied to a column of Bio-Gel P-2 (obtained from Bio-Rad Co.), concentrated, and then freeze-dried to obtain 50 milligrams of maltopentaose white powder.

EXAMPLE 2

The procedure of Example 1 was repeated wherein 2.5% of each polysaccharide as shown in Table 1 was used in place of the soluble starch. The results are shown in Table 1. The yield of maltopentaose was 40–60%.

TABLE 1

| Carbon Source | Concentration of Carbohydrate (mg/ml) | Concentration of Maltopentaose (mg/ml) | Ratio (%) |
| --- | --- | --- | --- |
| Amylose (potato, produced by Wako Junyaku Co., Ltd.) | 0.5 | — | — |
| Amylose ($\overline{DP}$ = 17, produced by Hayashibara Co., Ltd.) | 15.2 | 7.8 | 51 |
| Amylose ($\overline{DP}$ = 100, produced by Hayashibara Co., Ltd.) | 2.8 | 2.2 | 79 |
| Amylopectin (potato, produced by Shigma Co., Ltd.) | 20.5 | 7.7 | 38 |
| Dextrin (produced by Kanto Kagaku Co., Ltd.) | 24.3 | 5.2 | 21 |

EXAMPLE 3

Ten liters of a medium (pH: 8.0) containing 2.5% soluble starch, 1% peptone, and 0.5% NaCl was placed in a 30-liter jar fermentater and sterilized at 121° C. for 10 minutes. 100 Milliliters of a suspension of *Bacillus* cereus NY-14 (deposited in the Fermentation Research Institute, Japan, under the accession number of FERM BP-329) which had previously been cultivated in the same medium as above, was used as an inoculum into 30 liter jar fermenter (rotation of impeller at 150 rpm and the aeration at 10 liters per minute).

After incubation at 30° C. for 48 hours, the culture broth was centrifuged at 4° C. at 6,000 rpm to remove the bacterial cells. In the thus-obtained supernatant, the concentration of carbohydrate was 16.4 milligrams per milliliter and the concentration of maltopentaose was 6.2 milligrams per milliliter, and 38% of the residual saccharides could be accumulated as maltopentaose.

One liter of the above-obtained supernatant was processed in the same manner as in Example 1 to obtain 3.5 grams of maltopentaose white powder.

What is claimed is:

1. A process for preparing maltopentaose which comprises cultivating the maltopentaose-producing microorganism Bacillus cereus NY-14 (FERM BP-329) in a medium comprising a polysaccharide having an α-1,4-glucosidic linkage to produce and accumulate maltopentaose in a culture broth, and recovering the maltopentaose therefrom.

2. The process of claim 1, wherein said cultivating to produce and accumulate maltopentaose is carried out under aerobic conditions.

3. The process of claim 2, wherein sid medium also contains an organic or inorganic nitrogen source.

4. The process of claim 2, wherein said polysaccharide is a substance selected from the group consisting of starch, soluble starch, amylopectin, amylose, dextrin and a mixture thereof.

5. The process of claim 4, wherein said medium contains between 2.5 and 4% polysaccharide and the cultivation is carried out at a pH of from 7.0 to 8.0 and at a temperature of from 25° to 30° C.

6. The process of claim 5 wherein said medium also contains an organic or inorganic nitrogen source.

7. The process of claim 4, wherein said medium also contains an organic or inorganic nitrogen source.

8. The process of claim 1, wherein said medium contains between 0.5 and 40% polysaccharide and the cultivation is carried out at a pH of from 5.5 to 9.0 and at a temperature of from 20° to 37° C.

9. The process of claim 8, wherein said medium also contains an organic or inorganic nitrogen source.

10. The process of claim 1, wherein said medium also contains an organic or inorganic nitrogen source.

* * * * *